US010927068B2

(12) United States Patent
Orr et al.

(10) Patent No.: US 10,927,068 B2
(45) Date of Patent: Feb. 23, 2021

(54) PROCESS FOR PREPARING ACYLATED AMPHETAMINE DERIVATIVES

(71) Applicant: SpecGX LLC, Webster Groves, MO (US)

(72) Inventors: Brian Orr, Webster Groves, MO (US); Kevin Roesch, Webster Groves, MO (US); Joel McClenaghan, Webster Groves, MO (US)

(73) Assignee: SpecGX LLC, Webster Groves, MO (US)

( * ) Notice: Subject to any disclaimer, the term of this patent is extended or adjusted under 35 U.S.C. 154(b) by 0 days.

(21) Appl. No.: 16/201,645

(22) Filed: Nov. 27, 2018

(65) Prior Publication Data

US 2019/0161435 A1  May 30, 2019

Related U.S. Application Data

(60) Provisional application No. 62/592,503, filed on Nov. 30, 2017.

(51) Int. Cl.
| | |
|---|---|
| *C07C 231/10* | (2006.01) |
| *C07C 231/24* | (2006.01) |
| *C07C 269/08* | (2006.01) |
| *C07C 269/06* | (2006.01) |
| *C07C 231/02* | (2006.01) |
| *C07C 231/12* | (2006.01) |

(52) U.S. Cl.
CPC .......... *C07C 231/10* (2013.01); *C07C 231/02* (2013.01); *C07C 231/12* (2013.01); *C07C 231/24* (2013.01); *C07C 269/06* (2013.01); *C07C 269/08* (2013.01); *C07B 2200/07* (2013.01)

(58) Field of Classification Search
None
See application file for complete search history.

(56) References Cited

U.S. PATENT DOCUMENTS

2009/0234002 A1*  9/2009  Mickle ............... C07C 237/06
                                                         514/483
2011/0196173 A1   8/2011  Meudt
2012/0157706 A1   6/2012  Bauer
2012/0190880 A1   7/2012  Jass

FOREIGN PATENT DOCUMENTS

WO  WO 2013011526  *  1/2013
WO      2017/003721 A1    1/2017

OTHER PUBLICATIONS

Kano et al., "Thirteen-week oral toxicity of 1,4-dioxane in rats and mice", The Journal of Toxicological Sciences, 2008, 33 (2), 141-153.
Kasai et al, "Thirteen-week inhalation toxicity of 1,4-dioxane in rats", Inhalation Toxicology, 2008, 20 (10), 961-971.
Kasai et al., "Two-year inhalation study of carcinogenicity and chronic toxicity of 1,4-dioxane in male rats", Inhalation Toxicology, 2009, 21 (11), 889-897.
International Search Report and Written Opinion dated Jan. 16, 2019 in related International Application No. PCT/US2018/062624, 8 pp.
Dichloromethane (Methylene Chloride) Hazards & Safety Information, MSDSOnline, Feb. 20, 2015, 8 pages, https://www.msdsonline.com/2015/02/20/dichloromethane-methylene-chloride-hazards-safety-information/.
Sodium bicarbonate, PubChem, Mar. 27, 2005, 2 pages, https://pubchem.ncbi.nlm.nih.gov/compound/Sodium-bicarbonate#.

* cited by examiner

*Primary Examiner* — Sudhakar Katakam
*Assistant Examiner* — Jennifer C Sawyer

(57) ABSTRACT

Processes for preparing acetylated amphetamine derivatives and, in particular, processes for preparing L-lysine-D-amphetamine dimesylate from D-amphetamine salts.

17 Claims, No Drawings

PROCESS FOR PREPARING ACYLATED AMPHETAMINE DERIVATIVES

CROSS-REFERENCE TO RELATED APPLICATIONS

This application claims the priority of U.S. Provisional Application Ser. No. 62/592,503, filed Nov. 30, 2017, the disclosure of which is hereby incorporated by reference in its entirety.

FIELD

The present disclosure generally relates to processes for preparing acetylated amphetamine derivatives and, in particular, processes for preparing L-lysine-D-amphetamine dimesylate.

BACKGROUND

L-lysine-D-amphetamine dimesylate (also called lisdexamphetamine dimesylate) is used to treat attention deficit hyperactivity disorder (ADHD) and attention deficit disorder (ADD) in adults and children 6 years of age and older. This pharmaceutical is also used to treat moderate to severe binge eating disorder (BED). It belongs to the group of medicines called central nervous system (CNS) stimulants. D-amphetamine is the active metabolite of the prodrug lisdexamphetamine dimesylate. The D-amphetamine is liberated from lisdexamphetamine enzymatically following contact with red blood cells. The conversion is rate-limited by the enzyme, which prevents high blood concentrations of D-amphetamine and reduces the abuse potential of lisdexamphetamine at clinical doses.

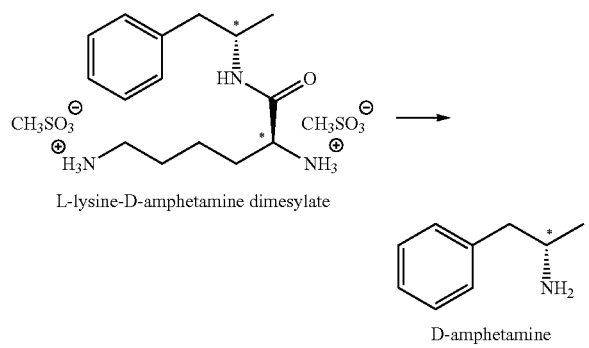

L-lysine-D-amphetamine dimesylate

D-amphetamine

Processes exist for the preparation of lisdexamphetamine dimesylate at laboratory scale. A need exists for a simple, inexpensive industrial process to make the latter scalable (e.g., no chromatography or rotary evaporation involved or isolation of problematic intermediates with difficult handling properties with respect to drying and recrystallization).

SUMMARY

One aspect of the present disclosure encompasses a one-pot process for preparing a compound of Formula (IV), which is an acylated amphetamine derivative. The process comprises (a) forming a reaction mixture comprising a solvent and a compound of Formula (I), the solvent being an alkyl tetrahydrofuran; (b) adding a compound of Formula (II) to the reaction mixture, thereby forming an intermediate compound of Formula (III); (c) phase extracting the reaction mixture after step (b) with one or more aqueous solutions to remove the compounds of Formulas (I) and (II) and reaction by-products, thereby forming a purified mixture comprising the intermediate compound of Formula (III); and (d) contacting the purified mixture comprising the intermediate compound of Formula (III) with an acid to form the compound of Formula (IV). The compounds of Formulas (I), (II), (III), and (IV) having the following structures:

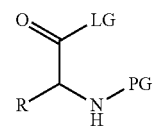

(I)

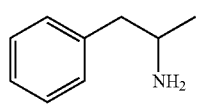

(II)

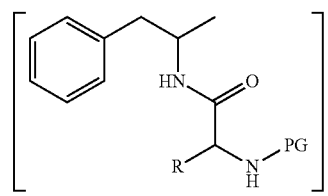

(III)

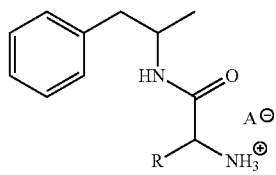

(IV)

wherein:
R is hydrocarbyl or substituted hydrocarbyl;
LG is a leaving group;
PG is a protecting group; and
A is an anion.

Another aspect of the present disclosure provides a one-pot process for preparing L-lysine-D-amphetamine dimesylate. The process comprises (a) converting a D-amphetamine salt to D-amphetamine; (b) adding D-amphetamine to a reaction mixture comprising 2-methyl tetrahydrofuran and N,N'-di-Boc-L-lysine hydroxysuccinimide ester to form an intermediate compound, the intermediate compound being N,N'-di-Boc-L-lysine-D-amphetamine; (c) phase extracting the reaction mixture after step (b) with one or more aqueous solutions to remove starting reactants and reaction by-products, thereby forming a purified mixture comprising the intermediate compound; and (d) contacting the purified mixture comprising the intermediate compound with methanesulfonic acid to form L-lysine-D-amphetamine dimesylate.

Other aspects and iterations of the disclosure are described in more detail below.

DETAILED DESCRIPTION

The present disclosure provides a simplified one-pot process to prepare crude L-lysine-D-amphetamine dimesylate (lisdexamphetamine dimesylate) from D-amphetamine salts. The protected intermediate formed during the synthesis process is purified by a series of extractions (thus, eliminating the need for expensive, industrial chromatography and isolation of a problematic intermediate), dried by azeotropic distillation. No isolation is carried out until a crude lisdexamphetamine dimesylate is obtained. The crude lisdexamphetamine dimesylate is further purified by recrystallization, which includes a polishing filtration to remove any insoluble material. Cooling and isolation leads to very pure material. The process described herein has industrial applicability, with further improvements to yield (e.g., minimal isolations) and safety (e.g., elimination of toxic solvents such as 1,4-dioxane).

(I) Process for Preparing Acylated Amphetamine Derivatives

One aspect of the present disclosure provides a one-pot process for preparing an acylated amphetamine derivative having Formula (IV). The process comprises (a) forming a reaction mixture comprising a solvent and a compound of Formula (I), the solvent being an alkyl tetrahydrofuran; (b) adding a compound of Formula (II) to the reaction mixture, thereby forming an intermediate compound of Formula (III); (c) phase extracting the reaction mixture after step (b) with one or more aqueous solutions to remove the compounds of Formulas (I) and (II) and reaction by-products, thereby forming a purified mixture comprising the intermediate compound of Formula (III); and (d) contacting the purified mixture comprising the intermediate compound of Formula (III) with an acid to form the compound of Formula (IV), as shown in the reaction scheme below.

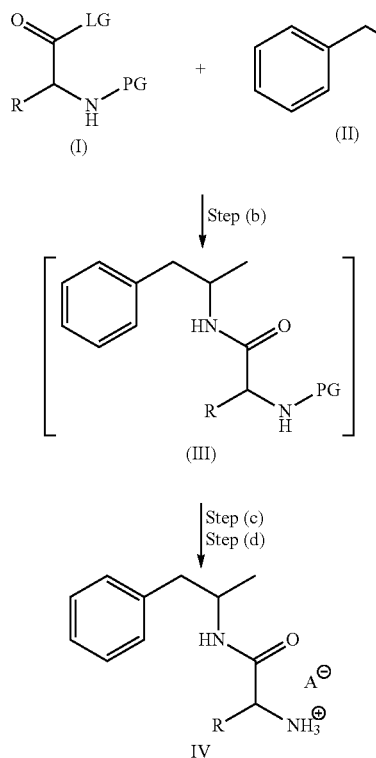

wherein:
R is hydrocarbyl or substituted hydrocarbyl;
LG is a leaving group;
PG is a protecting group; and
A is an anion.

The various steps of the process are detailed below.

(a) Forming a Reaction Mixture

The first step of the process comprises forming a reaction mixture comprising a compound of Formula (I) and a solvent.

(i) Compound of Formula (I)

The compound of Formula (I) comprises a carbonyl group, a leaving group (LG), an R group, and an amino group. In general, the amino group is protected with a protecting group (PG). Non-limiting examples of suitable amino protecting groups include tert-butyloxycarbonyl (Boc), triphenylmethyl (trityl), dimethyl-3,5-dimetheoxy-benzyloxycarbonyl (Ddz), 2-(4-biphenyl)isopropoxycarbonyl (Bpoc), 2-nitropheylsulfenyl (Nps), 2-chlorobenzyloxycarbonyl (Cl-Z), or 4-methyltrityl (Mtt). In specific embodiments, the protecting group may be tert-butyloxycarbonyl.

In various embodiments, R in the compound of Formula (I) may be alkyl, substituted alkyl, alkenyl, substituted alkenyl, alkylamino, substitute alkyamino, alkylhydroxy, substituted alkylhydroxy, alkylthio, substituted alkylthio, alkylaryl, or substituted alkyl aryl. In some embodiments, R may be an amino acid side chain. For example, R may be $-(CH_2)_4-NH_2$, $-(CH_2)_3-NH-C(NH)-NH_2$, $-(CH_2)_4-NH-C(NH)-NH_2$, $-CH_2-C(O)-NH_2$, $-(CH_2)_2-C(O)-NH_2$, $-CH_2-SH$, $-CH_2-OH$, $CH(OH)-CH_3$, $-CH_2-Ph-OH$, $-CH2-C(O)-OH$, or $-(CH_2)_2-C(O)-OH$. In exemplary embodiments, R may be $-(CH_2)_4-NH_2$.

In embodiments in which R is an amino acid side chain, the terminal group of the side chain may be protected with a protecting group. Suitable amino protecting groups are listed above. Non-limiting examples suitable hydroxy protecting groups include benzoyl, β-methyoxyethoxymethyl ether (MEM), methoxymethyl ether (MOM), p-methoxybenzyl ether (PMB), or pivaloyl.

The compound of Formula (I) also comprises a leaving group that facilitates amide coupling of the compounds of Formulas (I) and (II). In specific embodiments, the leaving group may be N-hydroxysuccinimidyl. In other embodiments, the leaving group may be halo, e.g., chloro, fluoro, or bromo.

In specific embodiments, the compound of Formula (I) is a compound of Formula (Ia):

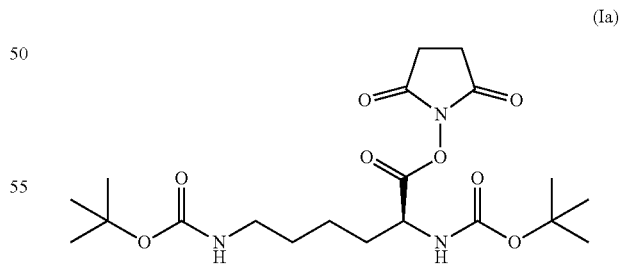

(ii) Solvent

In general, the solvent is a solvent having limited miscibility in water. Suitable solvents include alkyl tetrahydrofurans, benzene, n-butanol, butyl acetate, cyclohexane, 1,2-dichloroethane, dichloromethane, ethyl acetate, di-ethyl ether, heptane, hexane, methyl-t-butyl ether, methyl ethyl ketone, pentane, di-iso-propyl ether, toluene, and xylene. In specific embodiments, the solvent may be an alkyl tetrahydrofuran such as 2-methyl tetrahydrofuran or 3-ethyl tetrahydrofuran. In exemplary embodiments, the solvent may be 2-methyl tetrahydrofuran.

The amount of solvent added to the reaction mixture can and will vary. In general, the weight ratio of the solvent to the compound of Formula (I) may range from about 2:1 to about 50:1. In some embodiments, the weight ratio of the solvent to the compound of Formula (I) may range from about 3:1 to about 20:1, from about 4:1 to about 20:1, from about 5:1 to about 15:1, or from about 6:1 to about 10:1.

(b) Adding a Compound of Formula (II) to the Reaction Mixture

Step (b) of the process comprises adding a compound of Formula (II) to the reaction mixture. The compound of Formula (II) a free base of an amphetamine. In specific embodiments, the compound of Formula (II) is D-amphetamine, which is a compound of Formula (IIa):

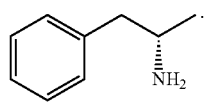
(IIa)

In some embodiments, the compound of Formula (II) may be prepared from an amphetamine salt. Non-limiting examples of suitable amphetamine salts include amphetamine bitartrate, amphetamine sulfate, amphetamine aspartate, amphetamine saccharate, amphetamine hydrochloride, and amphetamine phosphate. In specific embodiments, the amphetamine salt may be amphetamine bitartrate. The amphetamine salt may be converted to the free base by contact with a base, followed by extraction with the solvent used in the process. Suitable bases include, without limit, hydroxides of alkali metals and alkaline earth metals such as, e.g., sodium hydroxide or potassium hydroxide. In exemplary embodiments, the amphetamine salt may be contacted with a hydroxide, followed by several extractions with 2-methyl tetrahydrofuran. The 2-methyl tetrahydrofuran phases (comprising the compound of Formula (II)) may be combined and added to the reaction mixture formed in step (a).

In general, the amount of the compound of Formula (II) added to the reaction mixture is about equimolar to the amount of Formula (I) present in the reaction mixture. In various embodiments, the molar ratio of the compound of Formula (II) to the compound of Formula (I) may range from about 0.8:1.0 to about 1.2:1.0, from about 0.9:1.0 to about 1.1:1.0, or from about 0.95:1.00 to about 1.05:1.00.

The reaction between the compounds of Formula (I) and Formula (II) to form the intermediate compound of Formula (II) proceeds readily at ambient or room temperature. Importantly, the reaction proceeds without the addition of an organic base or an inorganic base. The reaction mixture may be stirred and maintained at ambient or room temperature for at least about 45 minutes, at least about 2 hours, at least about 6 hours, at least 12 hours, at least about 16 hours, or at least about 24 hours.

(c) Phase Extracting the Final Reaction Mixture

Step (c) of the process comprises extracting the final reaction mixture with one or more aqueous solutions to remove the compounds of Formulas (I) and (II), remove reaction by-products (e.g., the leaving group), and organic or inorganic salts, thereby forming a purified mixture comprising the intermediate compound of Formula (III). Importantly, the intermediate compound of Formula (III) is not isolated from the final reaction mixture after step (b) or the purified mixture following the phase extractions of step (c).

In some embodiments, the phase extractions comprise sequential contact with a water solution, an acid solution having a pH of less than about 3, an alkaline solution having a pH of greater than about 12, and one or more additional water solutions. After each extraction the aqueous phase is removed and discarded. In general, the phase extractions are conducted at ambient or room temperature.

The final purified mixture comprising the alkyl tetrahydrofuran solvent and the intermediate compound of Formula (III) may be azeotropically dried at reflux until the water content of the mixture is less than about 2%, or less than about 1% by weight (Karl Fischer). The final mixture may be diluted with the same solvent used in step (a). For example, the final mixture may be diluted with the solvent until the concentration of the intermediate compound of Formula (III) ranges from about 8% to about 12% by weight. In specific embodiments, the final mixture may be diluted with 2-methyl tetrahydrofuran until the concentration of the intermediate compound of Formula (III) is about 10% by weight.

(d) Contacting the Intermediate Compound with an Acid

Step (d) of the process comprises contacting the purified mixture comprising the intermediate compound of Formula (III) with an acid to form the compound of Formula (IV). Contact with the acid removes the protecting group(s) from the intermediate compound of Formula (III) and forms an acid salt of the compound. Non-limiting examples of suitable acids include methanesulfonic acid, hydrochloric acid, oxalic acid. In specific embodiments, the acid may be methanesulfonic acid.

The amount of acid added to the purified mixture comprising the intermediate compound of Formula (III) can and will vary. In general, the molar ratio of the acid to the intermediate compound of Formula (III) may range from about 1:1 to about 10:1. In some embodiments, the molar ratio of the acid to the intermediate compound of Formula (III) may range from about 2:1 to about 6:1, or from about 3:1 to about 4:1.

Contact with the acid is generally conducted at a temperature ranging from about 40° C. to about 70° C. In some embodiments, the temperature may range from about 40° C. to about 50° C., from about 50° C. to about 60° C., or from about 60° C. to about 70° C. In specific embodiments, contact with the acid may be conducted at about 50° C. to about 60° C. The duration of contact with acid at the elevated temperature may proceed for at least about 4 hours, at least about 6 hours, at least about 8 hours, at least about 10 hours, or at least about 12 hours.

The mixture may than be cooled to ambient or room temperature. The compound of Formula (IV) may be isolated from the solvent/acid mixture by filtration, centrifugation, or other suitable means. In some embodiments, the compound of Formula (IV) may be isolated by filtration. The filtration may be accomplished using a Büchner funnel, a filter funnel, or other filter aid. The filtration may be gravity filtration or vacuum filtration. The filtered product may be washed with the solvent used in the process. The final product may be dried at a temperature ranging from about 50° C. to about 70° C. for about 0.5 to about 2 hours in a vacuum oven or a drying oven.

(e) Recrystallizing the Compound of Formula (IV)

In some embodiments, the process further comprises recrystallizing the compound of Formula (IV). In general, the isolated compound of Formula (IV) is mixed with a suitable solvent to form a saturated solution. Non-limiting examples of suitable solvents include isopropanol, benzene, butanol, ethanol, ethyl acetate, heptane, methanol, methyl-t-butyl ether, octane, tetrahydrofuran, toluene, combinations thereof, and mixtures of any of the forgoing and water. In some embodiments, the solvent may be a mixture of isopropanol and water. In other embodiments, the solvent may be (100%) ethanol. The temperature of the saturated solution may be increased to about 70° C. to enable a polishing filtration to remove insolubles and then cooled to about 4° C. over a period of time. The crystallized compound of Formula (IV) may be isolated by filtration. The filtered compound may washed with the solvent used during the recrystallization process. The polished crystallized compound of Formula (IV) may be dried at a temperature ranging from about 50° C. to about 70° C. in a vacuum oven or a drying oven. The drying may proceed for at least 6 hours, at least 12 hours, at least 18 hours, or at least 24 hours.

In general, the yield of the compound of Formula (IV) prepared by the process disclosed herein may be at least about 80%, at least about 85%, at least about 90%, or at least about 95% by weight.

(f) Exemplary Embodiment

In some embodiments, the compounds of Formulas (I), (II), (III), and (IV) are compounds of Formulas (Ia), (IIa), (IIIa), and (IV), as shown in the reaction scheme below.

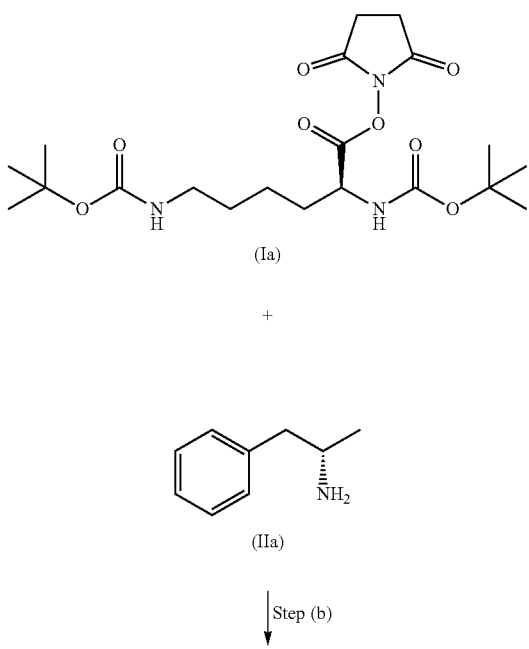

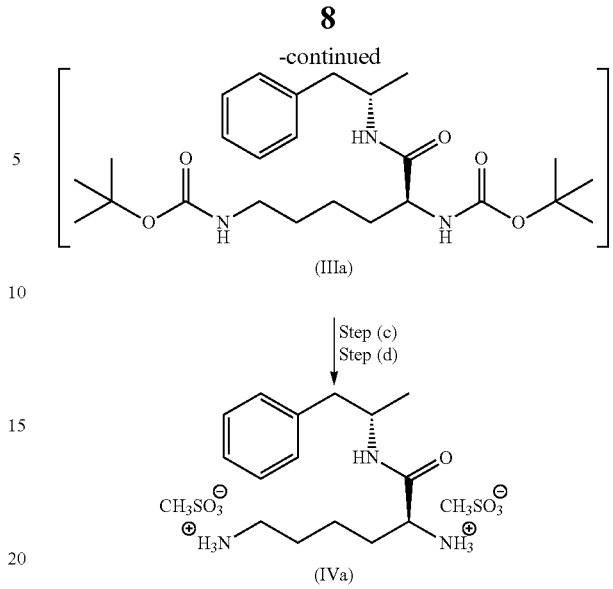

(II) Process for Preparing L-Lysine-D-Amphetamine Dimesylate

Another aspect of the present disclosure encompasses a one-pot process for preparing L-lysine-D-amphetamine dimesylate (i.e., the compound of Formula (IVa)). The process comprises (a) converting a D-amphetamine salt to D-amphetamine; (b) adding D-amphetamine to a reaction mixture comprising 2-methyl tetrahydrofuran (i.e., 2-MeTHF) and N,N'-di-Boc-L-lysine hydroxysuccinimide ester (i.e., a protected lysine) to form an intermediate compound, the intermediate compound being N,N'-di-Boc-L-lysine-D-amphetamine; (c) phase extracting the reaction mixture after step (b) with one or more aqueous solutions to remove starting reactants and reaction by-products, thereby forming a purified mixture comprising the intermediate compound; and (d) contacting the purified mixture comprising the intermediate compound with methanesulfonic acid to form L-lysine-D-amphetamine dimesylate.

Step (a) comprises contacting the D-amphetamine salt with an alkali metal or alkaline earth metal hydroxide, followed by one or more extractions with 2-methyl tetrahydrofuran. The reaction mixture of step (b) is formed by mixing the protected lysine with 2-MeTHF. The weight ratio of 2-MeTHF to the protected lysine may range from about 6:1 to about 10:1, or about 7:1. Step (b) comprises adding an approximately equimolar amount of D-amphetamine to the protected lysine. Step (b) is allowed to proceed at ambient or room temperature, during which the intermediate compound is formed.

The intermediate compound is not isolated. Rather the final reaction mixture comprising the intermediate compound is purified via a series of phase extractions during step (c). In particular, the extractions comprise sequential contact with a water solution (which removes the hydroxysuccinimide residue released from the protected lysine during the coupling reaction), an acid solution having a pH of less than about 3 (which removes the unreacted D-amphetamine and hydroxysuccinimide residues), an alkaline solution having a pH of greater than about 12 (which removes the unreacted protected lysine), and one or more additional water solutions (which remove organic and inorganic salts). After each extraction the aqueous phase is removed and discarded. The final purified mixture comprises the intermediate compound with little or no starting materials or reaction by-products.

The purified mixture comprising the intermediate compound is azeotropically dried at reflux (e.g., about 80-85° C.) until the water content is less than about 1% by weight (Karl Fischer). The resulting distillate is cooled to about 50-60° C. and the concentration of the intermediate compound is adjusted to about 10% by addition of 2-MeTHF. Step (d) comprises maintaining the temperature at about 50-60° C. while adding about 3-4 equivalents of methanesulfonic acid. The temperature is maintained at about 50-60° C. for at least 6-8 hours to ensure complete deprotection of the intermediate compound and formation of L-lysine-D-amphetamine dimesylate.

The final compound is isolated by filtration, washed with 2-MeTHF, and dried. L-Lysine-D-amphetamine dimesylate is recrystallized from a mixture of isopropanol and water, and polished by washing the crystallized material with isopropanol. The crystallization step removes undesirable diastereomers, and provides highly pure L-lysine-D-amphetamine dimesylate.

Definitions

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1: Preparation of D-Amphetamine Stock Solution

D-Amphetamine bitartrate (20.00 g, 0.0701 mol) was suspended in water (40.00 g). To this was added 50 wt. % sodium hydroxide (~7.25 mL) and 2-MeTHF (30 mL) to adjust aqueous phase to a pH>13. The actual pH obtained of the aqueous phase was 13.59 at 34.9° C. The organic phase was separated and the aqueous phase was further extracted (separatory funnel) with 2-MeTHF (90 mL). The organic phases were combined and used directly in the next example, no drying was required.

Example 2: Preparation of Crude Lisdexamphetamine Dimesylate Via 'One-Pot' Procedure Di-N-Boc-L-lysine-O-Su (31.09 g, 0.0701 mol) was slurried in 2-MeTHF (160 mL) at room temperature. To this, the D-amphetamine stock solution from Example 1 was charged to the reaction in one shot. The reaction was exothermic (e.g., the temperature rose from 20.7° C. to 29.1° C.). The reaction mixture was left to stir at room temperature for 16 hours. The reaction mixture was then quenched with water (46 mL) and the lower phase removed. The 2-MeTHF phase was further successively washed with 2 mL of concentrated hydrochloric acid in water (46 mL) (the pH of aqueous extract was <3.00); 2 mL of 50 wt. % sodium hydroxide (the pH of extract was >12.00); and water (46 mL) three times to remove salts. The 2-MeTHF phase remaining in the flask was set-up for azeotropic distillation using a Dean & Stark apparatus to remove water at a jacket temperature of 80-85° C. for 16 hours in this case. This removed 7.0 mL of water, the 2-MeTHF remaining typically had <1.00 wt. % of water remaining. The reaction was then cooled to 50-60° C. and diluted with 2-MeTHF (165 mL), such that the concentration of Di-N-Boc-L-lysine-D-amphetamine was at 10 wt. %/v based upon 100% yield of lisdexamphetamine dimesylate (i.e., 32.50 g in this example). Methanesulfonic acid (20.21 g, 0.2103 mol) was added such that the temperature was maintained between 50-60° C.; the reaction mixture was then held at this temperature to ensure complete deprotection for a least 6-8 hours. The reaction mixture was then cooled to room temperature and filtered on a Büchner funnel and washed with 2-MeTHF (50 mL). After air drying for 1 hour, the crude (30.69 g) was dried in a vacuum oven at 60° C., 22" Hg. This afforded crude lisdexamphetamine dimesylate as a white solid (30.25 g. 94.70% 'as-is', typically assaying at >95 wt. %, with the excess being excess methanesulfonic acid and solvents, etc.).

Example 3: Preparation of Pure Lisdexamphetamine Dimesylate

An aliquot (20.00 g) of the crude lisdexamphetamine dimesylate from the Example 2 was recrystallized from isopropanol (160.00 g) and water (5.00 g) with a polishing filtration. Material crystallized at 63.9° C. Left to cool to room temperature and ice cooling applied at 32.5° C. After stirring at <5° C. for 30 min, product was filtered and washed with isopropanol (15.00 g). This afforded a white powder friable flakes 19.31 g (96.55% recovery). Material was oven dried overnight 60-65° C. at 22" Hg to afford the product (17.49 g, 87.45%). Material assayed at 99.57 wt. % with no related substances present. Rolled through-put yield=0.9470×0.8755×100=82.91%.

What is claimed is:

1. A process for preparing a compound of Formula (IV), the process comprising:
(a) forming a reaction mixture comprising a solvent and a compound of Formula (I), the solvent being an alkyl tetrahydrofuran;

(b) adding a compound of Formula (II) to the reaction mixture, thereby forming an intermediate compound of Formula (III);

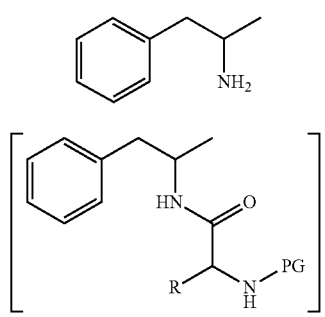

(II)

(III)

(c) phase extracting the reaction mixture after step (b) with (i) a water wash; (ii) an acid wash having a pH of <3.0, (iii) an alkaline wash having a pH of >12.0, and (iv) one or more additional water washes to remove the compounds of Formulas (I) and (II) and reaction by-products, thereby forming a purified mixture comprising the intermediate compound of Formula (III); and (d) contacting the purified mixture comprising the intermediate compound of Formula (III) with an acid to form the compound of Formula (IV);

(IV)

wherein:
R is hydrocarbyl or substituted hydrocarbyl;
LG is a leaving group chosen from N-hydroxysuccinimidyl or halo;
PG is a protecting group; and
A is an anion.

2. The process of claim 1, wherein R is an amino acid side chain chosen from —(CH$_2$)$_4$—NH$_2$, —(CH$_2$)$_3$—NH—C(NH)—NH$_2$, —(CH$_2$)$_4$—NH—C(NH)—NH$_2$, —CH$_2$—C(O)—NH$_2$, —(CH$_2$)$_2$—C(O)—NH$_2$, —CH$_2$—SH, —CH$_2$—OH, CH(OH)—CH$_3$, —CH$_2$-Ph-OH, —CH2-C(O)—OH, or —(CH$_2$)$_2$—C(O)—OH; and PG is tert-butyloxycarbonyl, triphenylmethyl, dimethyl-3,5-dimetheoxybenzyloxycarbonyl, 2-(4-biphenyl)isopropoxycarbonyl, 2-nitropheylsulfenyl, 2-chlorobenzyloxycarbonyl, or 4-methyltriphenymethyl.

3. The process of claim 1, wherein the alkyl tetrahydrofuran and the compound of Formula (I) are present in the reaction mixture at a weight ratio of about 5:1 to about 15:1; steps (b) and (c) are conducted at room temperature; the acid at step (d) is methanesulfonic acid, hydrochloric acid, or oxalic acid; and step (d) is conducted at a temperature from about 40° C. to about 70° C.

4. The process of claim 1, further comprising azeotropically drying the purified mixture comprising the intermediate compound of Formula (III) after step (c) until it has a water content of less than about 2% by weight.

5. The process of claim 1, further comprising isolating the compound of Formula (IV) after step (d) by filtration.

6. The process of claim 5, further comprising recrystallizing the compound of Formula (IV).

7. The process of claim 1, wherein the compound of Formula (I) is a compound of Formula (Ia):

(Ia)

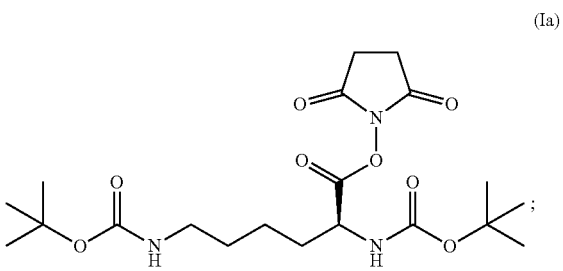 [SMILES: CC(C)(C)OC(=O)NCCCC[C@H](NC(=O)OC(C)(C)C)C(=O)ON1C(=O)CCC1=O]

the compound of Formula (II) is a compound of Formula (IIa):

(IIa)

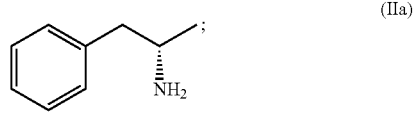

the intermediate compound of Formula (III) is a compound of Formula (IIIa), (IIIa)

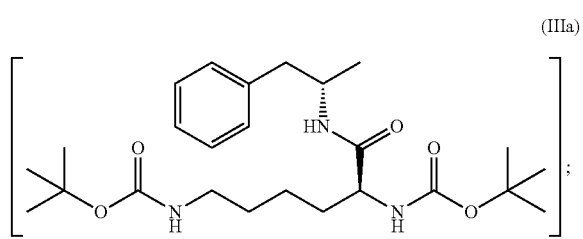

and
the compound of Formula (IV) is a compound of Formula (IVa):

(IVa)

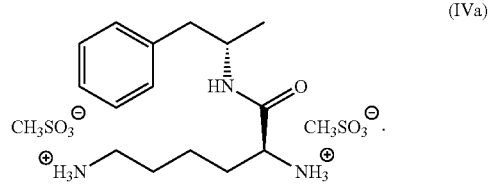

8. The process of claim 7, wherein the alkyl tetrahydrofuran at step (a) is 2-methyl tetrahydrofuran.

9. The process of claim 8, wherein 2-methyl tetrahydrofuran and the compound of Formula (Ia) are present in the reaction mixture at a weight ratio of about 6:1 to about 10:1.

10. The process of claim 9, wherein the compound of Formula (IIa) is prepared from a salt of a compound of Formula (IIa) by contacting the salt of the compound of Formula (IIa) with an alkali metal or alkaline earth metal hydroxide, followed by one or more extractions with 2-methyl tetrahydrofuran.

11. The process of claim 7, wherein steps (a) and (b) are conducted at room temperature; and step (d) is conducted at a temperature from about 50° C. to about 60° C.

12. The process of claim 7, wherein step (c) comprises sequential contact with a water solution, a solution of hydrochloric acid having a pH of less than about 3, a solution of sodium hydroxide having a pH of greater than about 12, and one or more additional water solutions.

13. The process claim 7, further comprising azeotropically drying the purified mixture comprising the intermediate compound of Formula (IIIa) after step (c) until it has a water content of less than about 1% by weight.

14. The process of claim 7, further comprising isolating the compound of Formula (IVa) by filtration after step (d).

15. The process of claim 14, further comprising recrystallizing the compound of Formula (IVa).

16. The process of claim 15, wherein the recrystallizing is conducted in the presence of a mixture of isopropanol and water.

17. The process of claim 15, further comprising washing the crystallized compound of Formula (IVa) with isopropanol.

* * * * *